United States Patent [19]

Allen et al.

[11] Patent Number: 5,587,468

[45] Date of Patent: Dec. 24, 1996

[54] HIGH AFFINITY NUCLEIC ACID LIGANDS TO HIV INTEGRASE

[75] Inventors: Patrick Allen; Larry Gold, both of Boulder, Colo.

[73] Assignee: University Research Corporation, Boulder, Colo.

[21] Appl. No.: 442,572

[22] Filed: May 16, 1995

Related U.S. Application Data

[63] Continuation of Ser. No. 361,795, Dec. 21, 1994, which is a continuation-in-part of Ser. No. 714,131, Jun. 10, 1991, Pat. No. 5,475,096, Ser. No. 964,624, Oct. 21, 1992, and Ser. No. 117,991, Sep. 8, 1993, said Ser. No. 714,131, is a continuation-in-part of Ser. No. 536,428, Jun. 11, 1990, abandoned.

[51] Int. Cl.$^6$ .......................... C07H 21/02; C07H 21/04; C12P 19/34; C12Q 1/68
[52] U.S. Cl. ..................... 536/22.1; 435/6; 435/91.2; 935/77; 935/78
[58] Field of Search .................................. 536/23.1, 22.1

[56] References Cited

U.S. PATENT DOCUMENTS

| 5,118,672 | 6/1992 | Schinazi et al. .......................... 435/6 |
| 5,270,163 | 12/1993 | Gold et al. .................................... 435/6 |

FOREIGN PATENT DOCUMENTS

| 2183661 | 6/1987 | United Kingdom . |
| WO89/06694 | 7/1989 | WIPO . |
| WO91/19813 | 12/1991 | WIPO . |
| WO92/03568 | 3/1992 | WIPO . |
| 9214843 | 9/1992 | WIPO .......................................... 435/6 |

OTHER PUBLICATIONS

Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Allen and Noller (1989) J. Mol. Biol. 208:457.
Barre–Sinoussi et al. (1983) Science 220:868.
Bartel et al. (1991) Cell 67:529.
Bowerman et al. (1989) Genes and Development 3:469.
Bushman and Craigie (1991) Proc. Natl. Acad. Sci. USA 88:1339.
Cann and Chen (1990) in *Virology* 2nd Ed. (B. N. Fields et al. eds) Raven Press, NY pp. 1501–1527.
Chastain and Tinoco (1991) Prog. Nucl. Acid Res. and Molec. Biol. 41:131.
Chen and Gold (1994) Biochem. 33:8746.
Chow and Brown (1994) J. Virol. 68:3896.
Chow et al. (1992) Science 255:723.
Craigie et al. (1990) Cell 62:829.
Donehower and Varmus (1984) Proc. Natl. Acad. Sci. USA 81:6461.

(List continued on next page.)

*Primary Examiner*—Stephanie W. Zitomer
*Attorney, Agent, or Firm*—Swanson & Bratschun LLC

[57] ABSTRACT

Methods are described for the identification and preparation of nucleic acid ligands to HIV integrase. Included in the invention are specific RNA ligands to HIV integrase identified by the SELEX method. Also included in the invention are specific RNA ligands that are inhibitors of HIV integrase.

16 Claims, 1 Drawing Sheet

OTHER PUBLICATIONS

Engelman et al. (1993) EMBO J. 12:3269.
Favorova et al. (1981) Biochem. 20:1006.
Gallo et al. (1983) Science 220:865.
Goff (1992) Ann. Rev. Genet. 26:527.
Grandgenett et al. (1986) J. Virol. 58:970.
Guschlbauer et al. (1977) Nucleic Acids Res. 4:1933.
Hobbs et al. (1973) Biochem 12:5138.
Jones et al. (1992) J. Biol. Chem. 267:16037.
Katzman et al. (1989) J. Virol. 63:5319.
Larder et al. (1989) Science 243:1731.
Leavitt et al. (1993) J. Biol. Chem. 268:2113.
Lockard and Kumar (1981) Nucleic Acids Res. 9:5125.
Moazed et al. (1986) J. Mol. Biol. 187:399.
Pieken et al. (1991) Science 253:314.
Schwartzberg et al. (1984) Cell 37:1043.
Shaw et al. (1984) Science 226:1165.
Sherman and Fyfe (1990) Proc. Natl. Acad. Sci. USA 87:5119.
Shibahara et al. (1987) Nucleic Acids Res. 15:4403.
Stern et al. (1988) Meth. Enzymol. 164:481.
Tuerk and Gold (1990) Science 249:505.
Tuerk et al. (1992) Proc. Natl. Acad. Sci. USA 89:6988.
Vaishnav and Wong–Staal (1991) Ann. Rev. Biochem. 60:577.
Whitcomb and Hughes (1992) Ann. Rev. Cell Biol. 8:275.
Wong–Staal (1990) in *Virology* 2nd Ed. (B. N. Fields et al. eds) Raven Press, NY pp. 1529–1543.
Wu and Marshall (1990) Biochem. 29:1730.

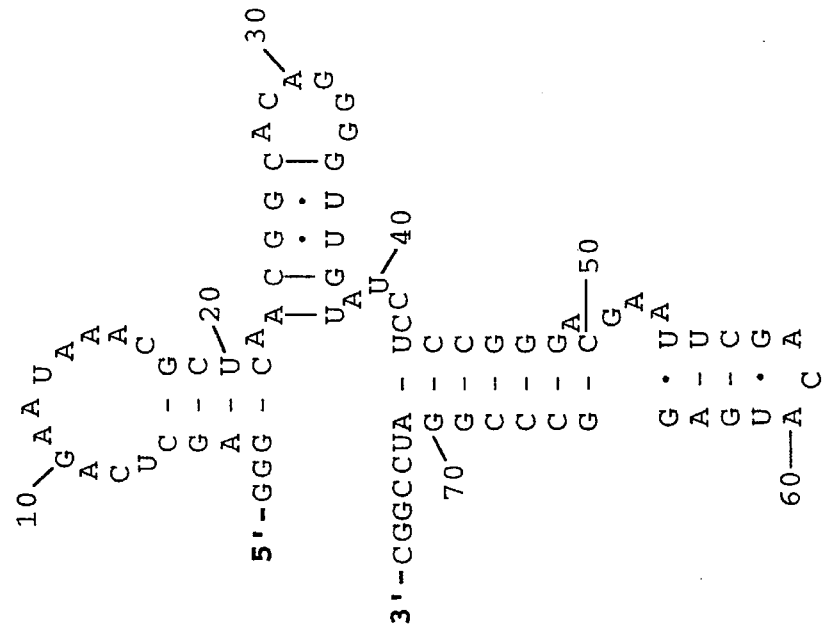
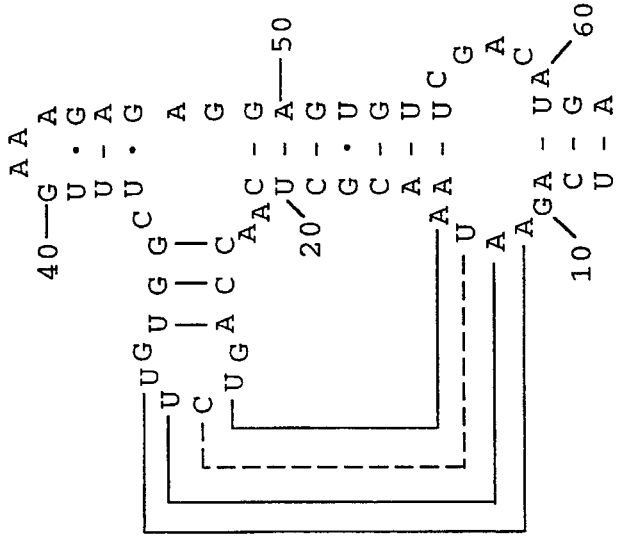
FIG. 1B
FIG. 1A

HIGH AFFINITY NUCLEIC ACID LIGANDS TO HIV INTEGRASE

This work was partially supported by grants from the United States Government funded through the National Institutes of Health (Grant Nos. GM42651, GM28685, and GM19963). The U.S. Government may have certain rights in this invention. This work was also supported in part by the Jane Coffin Childs Memorial Fund.

RELATED APPLICATIONS

This is a continuation of application Ser. No. 08/361,795 filed on Dec. 21, 1994, which is a Continuation-in-Part of U.S. patent application Ser. No. 07/714,131, filed Jun. 10, 1991, entitled Nucleic Acid Ligands, U.S. Pat. No. 5,475,096 U.S. patent application Ser. No. 07/964,624, filed Oct. 21, 1992, entitled Methods of Producing Nucleic Acid Ligands, and U.S. patent application Ser. No. 08/117,991, filed Sep. 8, 1993, entitled High-Affinity Nucleic Acid Ligands Containing Modified Nucleotides. U.S. patent application Ser. No. 07/714,131 is a Continuation-in-Part of U.S. patent application Ser. No. 07/536,428, filed Jun. 11, 1990, entitled Systematic Evolution of Ligands by EXponential Enrichment, now abandoned. U.S. patent application Ser. No. 07/931,473, filed Aug. 17, 1992, entitled Nucleic Acid Ligands, filed as a Divisional Application of U.S. application Ser. No. 07/714,131, issued as U.S. Pat. No. 5,270,163.

FIELD OF THE INVENTION

Described herein are methods for identifying and preparing high-affinity nucleic acid ligands to Human Immunodeficiency virus (HIV) integrase. For the purposes of this application, Human Immunodeficiency Virus integrase includes HIV Type 1 (HIV-1) integrase and HIV integrases that are substantially homologous thereto. By substantially homologous it is meant a degree of amino acid sequence homology of 80% or greater. The method utilized herein for identifying such nucleic acid ligands is called SELEX, an acronym for Systematic Evolution of Ligands by EXponential enrichment. Specifically disclosed herein are high-affinity RNA ligands. The invention includes high-affinity RNA inhibitors of HIV integrase.

BACKGROUND OF THE INVENTION

The causative agent for Acquired Immunodeficiency Syndrome (AIDS) is the Human Immunodeficiency Virus (Gallo et al. (1993) Science 220:865–867; Barre-Sinoussi et al. (1983) Science 220:868–870; Shaw et al. (1984) Science 226:1165–1171). Like all known retroviruses, HIV must reverse transcribe its RNA genome and integrate the double-stranded DNA copy into the host genome (for review; Wong-Staal (1990) In Virology 2nd Ed. (B. N. Fields et al. eds) Raven Press, N.Y. pp. 1529–1543; Cann and Chen (1990) In Virology 2nd Ed. (B. N. Fields et al. eds) Raven Press, New York pp. 1501–1527; Vaishnav and Wong-Staal (1991) Ann. Rev. Biochem. 60:577–630). The viral component that is essential for formation of a provirus is the integrase protein (Schwartzberg et al. (1984) Cell 37:1043–1052; Donebower and Varmus (1984) Proc. Natl. Acad. Sci. U.S.A. 81:6461–6465; Craigie et al. (1990) Cell 62:829–837). Integrase, in vitro, has been shown to be necessary and sufficient for processing of the double-stranded viral DNA (processing or donor cut; Katzman et al. (1989) J. Virol. 63:5319–5327; Sherman and Fyfe (1990) Proc. Natl. Acad Sci. U.S.A. 87:5119–5123), cleaving recipient DNA and ligating processed DNA to it (joining or strand transfer; Grandgenett et al. (1986) J. Virol. 58:970–974; Bushman and Craigie (1991) Proc. Natl. Acad. Sci. U.S.A. 88:1339–1343) and for an event that is yet to be demonstrated in vivo, resolution of integrated DNA to component parts (disintegration; Chow et al. (1992) Science 255:723–726; Chow and Brown (1994) J. Virol. 68:3896–3907). The protein has been divided into three structural domains. The N-terminal domain is highly conserved among retroviral integrases and encodes a Zn++ finger-like DNA binding motif. While the C-terminal domain is variable but consistently basic, with a net charge of about +11. Integrase associates with the double-stranded HIV DNA to form a pre-integration complex which is transported into the nucleus of infected cells (Bowerman et al. (1989) Genes and Development 3:469–478; reviews: Goff (1992) Ann. Rev. Genet. 26:527–544; Whitcomb and Hughes (1992) Ann. Rev. Cell Biol. 8:275–306). It has been suggested that integrase encodes a nuclear localization signal in the C-terminal domain. Mutational analysis of the different domains and the results from complementation tests suggest that integrase functions as a multimer rather than a monomer (Jones et al. (1992) J. Biol. Chem. 267:16037–16040; Engelman et al. (1993) EMBO J. 12:3269–3275; Leavitt et al. (1993) J. Biol. Chem. 268:2113–2119). This may explain how this enzyme is able to cleave different DNA sequences and remain associated with multiple ends of DNA at the same time.

A method for the in vitro evolution of nucleic acid molecules with high affinity binding to target molecules has been developed. This method, Systematic Evolution of Ligands by EXponential enrichment, termed SELEX, is described in U.S. patent application Ser. No. 07/536,428, entitled Systematic Evolution of Ligands by Exponential Enrichment, now abandoned, U.S. patent application Ser. No. 07/714,131, filed Jun. 10, 1991, entitled Nucleic Acid Ligands, U.S. patent application Ser. No. 07/931,473, filed Aug. 17, 1992, entitled Nucleic Acid Ligands, now U.S. Pat. No. 5,270,163 (see also PCT/US91/04078), each of which is herein specifically incorporated by reference. Each of these applications, collectively referred to herein as the SELEX Patent Applications, describe a fundamentally novel method for making a nucleic acid ligand to any desired target molecule.

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled Method for Selecting Nucleic Acids on the Basis of Structure, describes the use of SELEX in conjunction with gel electrophoresis to select nucleic acid molecules with specific structural characteristics, such as bent DNA. U.S. patent application Ser. No. 08/123,935, filed Sep. 17, 1993, entitled Photoselection of Nucleic Acid Ligands describes a SELEX based method for selecting nucleic acid ligands containing photoreactive groups capable of binding and/or photocrosslinking to and/ or photoinactivating a target molecule. U.S. patent application Ser. No. 08/134,028, filed Oct. 7, 1993, entitled High-Affinity Nucleic Acid Ligands That Discriminate Between Theophylline and Caffeine, describes a method for identifying highly specific nucleic acid ligands able to discriminate between closely related molecules, termed "counter-SELEX." U.S. patent application Ser. No. 08/143,564, filed Oct. 25, 1993, entitled Systematic Evolution of Ligands by EXponential Enrichment: Solution SELEX, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled High Affinity Nucleic Acid Ligands Containing Modified Nucleotides, that describes oligonucleotides containing nucleotide derivatives chemically modified at the 5- and 2'-positions of pyrimidines, as well as specific RNA ligands to thrombin containing 2'-amino modifications. U.S. patent application Ser. No. 08/134,028, supra, describes highly specific nucleic acid ligands containing one or more nucleotides modified with 2'-amino (2'—$NH_2$), 2'-fluoro (2'-F), and/or 2'-O-methyl (2'-OMe). Each of these applications is specifically incorporated herein by reference.

A SELEX-like process was used by Barrel et al. to identify the important structural features of the vira RNA element bound by the Rev protein of HIV-1. (Barrel et al. (1991) Cell 67:529–536.) In one of three rounds of selection performed, wild-type RNA was included in the reaction mixture to compete with the pool RNA for binding to the target protein.

The development of high affinity ligands capable of inhibiting HIV integrase would be useful in the treatment of Human Immunodeficiency Virus. Herein described are high affinity RNA ligand inhibitors of HIV integrase.

BRIEF SUMMARY OF THE INVENTION

The present invention includes methods of identifying and producing nucleic acid ligands to HIV integrase and the nucleic acid ligands so identified and produced. For the purpose of this application, Human Immunodeficiency Virus integrase includes HIV Type 1 (HIV-1) integrase and HIV integrases that are substantially homologous thereto. By substantially homologous it is meant a degree of amino acid sequence homology of 80% or more. Specifically, RNA sequences are provided that are capable of binding specifically to HIV integrase. Included within the invention are the RNA ligand sequences shown in Table 2 (SEQ ID NOS.:1–55).

Also included in this invention are RNA ligands of HIV integrase that are inhibitors of HIV integrase. Specifically, RNA ligands are identified and described which inhibit the viral DNA processing or encapsidation activities of HIV integrase.

Further included in this invention is a method of identifying nucleic acid ligands and nucleic acid ligand sequences to HIV integrase comprising the steps of (a) preparing a candidate mixture of nucleic acids, (b) partitioning between members of said candidate mixture on the basis of affinity to HIV integrase, and (c) amplifying the selected molecules to yield a mixture of nucleic acids enriched for nucleic acid sequences with a relatively higher affinity for binding to HIV integrase.

Also included in the invention is the method of identifying nucleic acid ligands and ligand sequences described above wherein the mixture contacted includes non-amplifiable random pool nucleic acids.

More specifically, the present invention includes the RNA ligands to HIV integrase identified according to the above-described method, including those ligands listed in Table 2 (SEQ ID NOS.:1–55). Also included are RNA ligands to HIV integrase that are substantially homologous to any of the given ligands and that have substantially the same ability to bind and inhibit HIV integrase. Further included in this invention are RNA ligands to HIV integrase that have substantially the same structural form as the ligands presented herein and that have substantially the same ability to bind and inhibit HIV integrase.

The present invention also includes modified nucleotide sequences based on the RNA ligands identified herein and mixtures of the same.

BRIEF DESCRIPTION OF THE FIGURE

FIG. 1A shows the proposed secondary structure of P5 RNA based on data from chemical probing experiments and computer modeling, and FIG. 1B shows the proposed secondary structure of A54 RNA based on data from chemical probing experiments and computer modeling.

DETAILED DESCRIPTION OF THE INVENTION

This application describes high-affinity oligonucleotide ligands to HIV integrase identified through the method known as SELEX. The SELEX method is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, U.S. patent application Ser. No. 07/931,473, filed Aug. 17, 1992, entitled Nucleic Acid Ligands, now U.S. Pat. No. 5,270,163, (see also WO 91/19813). These applications, each specifically incorporated herein by reference, are collectively called the SELEX Patent Applications.

in its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can by totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligand solutions obtained to a number of target species, including both protein targets where the protein is and is not a nucleic acid binding protein.

The methods described herein and the nucleic acid ligands identified by such methods are useful for both therapeutic and diagnostic purposes. Therapeutic uses include the treatment or prevention of diseases or medical conditions in human patients. Therapeutic uses may also include veterinary applications.

Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek for in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to HIV integrase described herein may specifically be used for identification of the HIV integrase protein.

SELEX provides high affinity ligands of a target molecule. This represents a singular achievement that is unprecedented in the field of nucleic acids research. The present invention applies the SELEX procedure to the specific target of HIV integrase. In the Example section below, the experimental parameters used to isolate and identify the nucleic acid ligands to HIV-1 integrase are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), methods are described for obtaining improved nucleic acid ligands after SELEX has been performed. The '624 application, entitled Methods of Producing Nucleic Acid Ligands, is specifically incorporated herein by reference.

In the present invention, a systematic evolution of ligands by exponential enrichment (SELEX) procedure was used to isolate RNAs with specific high affinity for HIV-1 integrase from a degenerate library containing 30 random positions (30N) (Examples 1 and 2). Secondary structure of selected ligands was predicted by computer analysis and chemical and enzymatic structure analysis (Example 3). RNA truncate studies of a selected ligand were performed to determine the minimal binding domain of the RNA (Example 4). In vitro inhibition of integrase is demonstrated in Example 5. A binding competition experiment demonstrated the ability of a selected ligand (P5) to be a potent competitive inhibitor of HIV-1 integrase (Example 6).

This invention includes the specific RNA ligands to HIV-1 integrase shown in Table 2 (SEQ ID NOS:1–55), identified by the method described in Examples 1–2. The scope of the ligands covered by this invention extends to all nucleic acid ligands of HIV integrase, modified and unmodified identified according to the SELEX procedure More specifically, this invention includes nucleic acid sequences that are substantially homologous to the RNA ligands shown in Table 2 (SEQ ID NOS.:1–55). By substantially homologous it is meant a degree of primary sequence homology in excess of 70%, most preferably in excess of 80%. A review of the sequence homologies of the RNA ligands of HIV-1 integrase shown in Table 2 shows that three groups of nucleic acid ligands have been identified. Within groups I and II, the sequences contain considerable homology, however in group III there is little sequence homology. There is very little or no sequence homology between members of the different groups of ligands identified, and therefore it is seen that sequences with little or no primary homology may have substantially the same ability to bind HIV integrase. For these reasons, this invention also includes nucleic acid ligands that have substantially the same structure and ability to bind HIV integrase as the nucleic acid ligands shown in Table 2. Substantially the same ability to bind HIV integrase means that the affinity is within one to two orders of magnitude of the affinity of the ligands described herein. It is well within the skill of those of ordinary skill in the art to determine whether a given sequence—substantially homologous to those specifically described herein—has substantially the same ability to bind HIV integrase.

This invention also includes the ligands as described above, wherein certain chemical modifications are made in order to increase the in vivo stability of the ligand or to enhance or mediate the delivery of the ligand. Examples of such modifications include chemical substitutions at the ribose and/or phosphate and/or base positions of a given nucleic acid sequence. See, e.g., Cook et al. PCT Application WO 92/03568; U.S. Pat. No. 5,118,672 of Schinazi et al.; Hobbs et al. (1973) Biochem. 12:5138; Guschlbauer et al. (1977) Nucleic Acids Res. 4:1933; Shibahara et al.; (1987) Nucleic Acids Res. 15:4403; Pieken et al. (1991) Science 253:314, each of which is specifically incorporated herein by reference. Such modifications may be made post-SELEX (modification of previously identified unmodified ligands) or by incorporation into the SELEX process.

As described above, because of their ability to selectively bind HIV integrase, the nucleic acid ligands to HIV integrase described herein are useful as pharmaceuticals. This invention, therefore, also includes a method for the treatment of HIV by administration of a nucleic acid ligand capable of binding to the HIV integrase.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parentoral administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following examples are provided to explain and illustrate the present invention and are not to be taken as limiting of the invention.

EXAMPLE 1

EXPERIMENTAL PROCEDURES

This Example provides general procedures followed and incorporated into the specific Examples that follow.

Materials.

HIV-1 integrase, isolated from BH10, was a generous gift from Agouron Pharmaceuticals, Inc., 3565 General Atomics Court, San Diego, Calif. 92121–1121. The BH10 clone is also publicly available from the AIDS Reagent Program, 685 Lofstrand Lane, Rockville, Md. 20850. Isolating and purifing HIV-1 integrase from BH10 would be routine for those skilled in the art. In addition, integrase (IIIB) can be purchased from Intracel Corporation, 359 Allston Street, Cambridge, Mass. 02139. DNA polymerase was purchased from Perkin Elmer Cetus. Alkaline Phosphatase (Calf intestinal) was purchased from Biolabs. T4 polynucleotide kinase was purchased from Boehringer. Cobra Venom Ribonuclease ($V_1$) was purchased from Pharmacia, and Ribonuclease $T_1$ was purchased from Boehringer. All other enzymes were purchased from commercial sources. pUC18 was purchased from BRL.

PCR Amplification and Selection.

SELEX was carried out essentially as described in the SELEX Patent Applications (see also Tuerk and Gold (1990) Science 249:505–510). A random pool of DNA $10^{14}$ oligomers was synthesized where the 5' and 3' proximal ends were fixed sequences used for amplification and the central region consisted of thirty randomized positions. (See Table 1 for the starting ssDNA template (SEQ. ID. NO. :57), the 3' PCR primer (SEQ. ID. NO.:58), and the 5' PCR primer (SEQ. ID. NO. :59) Ten picomoles of template were PCR amplified for 8 cycles in the initial round. Copy DNA of the selected pool of RNA from subsequent rounds of SELEX was PCR amplified 18 cycles. PCR reactions were carried out in 50 µl volume containing 200 picomoles of each primer, 2 mM final concentration dNTP's, 5 units of Thermus aquaticus DNA polymerase (Perkin Elmer Cetus) in a PCR buffer (10 mM Tris-Cl pH 8.4, 50 mM KCl, 7.5 mM $MgCl_2$, 0.05 mg/ml BSA). Primers were annealed at 58° C. for 20 seconds and extended at 74° C. for 2 minutes. Denaturation occurred at 93° C. for 30 seconds.

Products from PCR amplification were used for T7 in vitro transcription in a 200 µl reaction volume (Tuerk and Gold (1990) Science 249:505–510). T7 transcripts were purified from an 8 percent, 7M Urea polyacrylamide gel and eluted by crushing gel pieces in a Sodium Acetate/EDTA solution. For each round of SELEX, 50 picomoles of the selected pool of RNA was phosphatased for 30 minutes using Alkaline Phosphatase, Calf Intestinal (Biolabs). The reaction was then phenol extracted 3 times and chloroform extracted once, then ethanol precipitated. 25 picomoles of this RNA was 5' end-labeled using $\gamma$-$^{32}$P ATP with T4 polynucleotide kinase (Boehringer) for 30 minutes. Kinased RNA was gel purified and a small quantity (about 150 fmoles; 100,000 cpm) was used along with 250 picomoles of cold RNA to follow the fraction of RNA bound to integrase and retained on nitrocellulose filters during the separation step of SELEX. Typically a protein concentration was used that binds one to five percent of the total input RNA. A control (minus protein) was used to determine the background which is typically ≦0.1% of the total input. Selected RNA was eluted from filter by extracting three times with $H_2O$ saturated phenol containing 2% lauryl sulfate (SDS), 0.3M NaOAc and 5 mM EDTA followed by a chloroform extraction. Twenty five percent of this RNA was then used to synthesize cDNA for PCR amplification.

Selection with non-amplifiable Competitor RNA.

Selections were done using two buffer conditions where the only difference between the buffers is sodium concentration (250 mM NaCl or 500 mM NaCl). Two different buffer conditions were used to increase stringency (with the higher salt concentration being more stringent) and to determine whether different ligands would be obtained. After 10 rounds of SELEX, the binding constant of the selected pool decreased about an order of magnitude and remained constant for the next two additional rounds. Competitor RNA was not used in the first 12 rounds. After this round, the pool was split and selection was carried out in the presence and absence (control) of competitor RNA. For rounds 12 through 18, a 50-fold excess of a non-amplifiable random pool of RNA was present during selection to compete with non-specific low-affinity binders that may survive and thus be amplified. The competitor RNA, which had a 30N random region, was made as described supra for the amplifiable pool RNA; however, the competitor RNA had different primer annealing sequences (3'PCR primer, RNA reverse transcription primer: CCCGGATCCTCTTTACCTCTGT-GTG (SEQ ID NO.:60); 5'PCR primer, T7 promoter: CCGAAGCTTAATACGACTCACTATAGG-GACTATTGATGGCCTTCCGACC (SEQ ID NO.:61). Thus, the competitor tNA does not survive the cDNA synthesis or PCR amplification steps. It would be apparent to one skilled in the art that other primer sequences could be used as long as they were not homologous to those used for the pool RNA. The use of competitor RNA increased the affinity of the selected pool by several orders of magnitude. In addition, RNA sequencing of the selected pool after using competitor RNA in three rounds of selection (round 15 of SELEX) showed non-randomness in the sequence, whereas the pool of RNA that survived SELEX (round 15) with no competitor still appeared random. Control experiments where competitor RNA was used in the absence of selectable RNA produced no PCR product after 35 cycles of PCR amplification.

Cloning and Sequencing.

PCR amplified DNA from the round 18 selected-pool of RNA was phenol and chloroform extracted and ethanol precipitated. The extracted PCR DNA was digested using Bam HI and Hind III (Biolabs) and subcloned into pUC18. DNAs were phenol and chloroform extracted following digestion. Ligation was carried out at room temperature for two hours after which time the reaction was phenol and chloroform extracted and used to electroporate competent cells. Fifty transformants from the selections using competitor RNA at both NaCl concentrations were picked and their DNAs sequenced.

Chemical and Enzymatic Structure Probing.

RNAs were chemically modified using DMS (dimethyl sulfate), kethoxal (2-keto, 3-ethoxy-n-butryaldehyde) and CMCT (1-Cyclohexyl-3-(2-Morpholinoethyl)-Carbodiimide Metho-p-Toluene-sulfonate) and partially digested using Cobra Venom Ribonuclease ($V_1$; Pharmacia) and Ribonuclease $T_1$ (Boehringer) as described (Allen and Noller (1989) J. Mol. Biol. 208:457–468) with the following exceptions. Each modification reaction contains one of the following reagents, 2 µl of a 1:15 dilution of DMS in 100% ethanol; 4 µl of kethoxal at a concentration of 25 µg/µl in 50% ethanol; 25 µl of CMCT at 40 µg/µl in CMCT modification buffer (80 mM potassium borate (pH 8.0), 10 mM $MgCl_2$, 100 mM $NH_4Cl$); 2 µl of 0.01 unit/µl RNase $T_1$ and 2 µl of 0.001 unit/µl RNase $V_1$. Prior to modification, RNAs were incubated at 45° C. for 5 minutes in DMS and kethoxal modification buffer (80 mM potassium cacodylate (pH 8.0), 10 mM $MgCl_2$, 100 mM $NH_4Cl$) or CMCT modification buffer. Samples were then incubated for 20 minutes at 37° C. in the presence or absence of integrase protein. Chemical modifications were carried out in a reaction volume of 50 µl and were done at 37° C. for 8 minutes and enzymatic digestion for 3 minutes at the same volume and temperature. Each reaction contained 10 picomoles of RNA (0.25 µg). In reactions containing integrase, the integrase concentrations were $5 \times 10^{-7}$M or $1 \times 10^{-6}$M. RNAs that were digested with ribonucleases were done only in the absence of integrase. Modified RNAs were then phenol extracted twice and chloroform extracted once and primer extended (Stern et al. (1988) Meth. Enzymol. 164:481–489) to determine positions that were accessible to the probes. The positions are identified by a pause or stop by reverse transcriptase.

Binding Assays.

Binding assays were done by adding 5 µl of HIV-1 integrase protein, at the appropriate concentrations (i.e., ranging from $2 \times 10^{-6}$ with 3 fold dilutions to $9 \times 10^{-9}$ for 250 mM NaCl and $0.5 \times 10^{-7}$ with 3 fold dilutions to $2 \times 10^{-10}$ for 50 mM NaCl), to 45 µl of binding buffer (50 mM Na-HEPES pH 7.5, 250 mM NaCl, 2 mM DTT, 10 mM $MnCl_2$, 5 mM CHAPS) on ice, then adding 50,000 cpm of kinased RNA (<200 fmoles) in a volume of 3 to 4 µl. This mix is incubated at 37° C. for 20 minutes. The reactions were then passed over nitrocellulose filters, which were pre-equilibrated in buffer, and washed with a 50 mM Tris-Cl pH 7.5 solution. Filters were dried and counted in cocktail. The proteins used in these experiments were frozen and thawed only once. Each binding curve consisted of seven points and each point is an average since experiments were done in triplicate.

In Vitro Processing Assay.

Con(+) (5'-CAATGACCGCATGGGATCCGTGTG-GAAAATCTCTAGCAGT-3') (SEQ ID NO.:56) and Con(–) (5'-ACTGCTAGAGATTTTCCACACGGATC-CCATGCGGTCATTG-3') (the complement of SEQ. ID NO.:56) were the two DNA oligomers used to mimic the U5 region of the HIV-1 genome. Con(+) was end-labeled and annealed to Con(–) and the duplex purified on an 8% native acrylamide gel. The two strands were annealed by adding 2.5 fold excess of Con(–) strand to the Con(+) kinase reaction on ice and then heated immediately to 90° C. for 3 minutes and allowed to cool slowly to 40° C. then loaded on to gel. Purified duplex DNA was resuspended at 0.65 pmol/µl concentration. In a 10 µl reaction volume, 0.13 picomole of duplex DNA was incubated with integrase at $0.4 \times 10^{-5}$M in reaction buffer (50 mM Na-HEPES pH 7.0, 50 mM NaCl, 2 mM DTT, 2.5 mM $MgCl_2$) for 20 minutes at 37° C. When inhibitor RNA was present in reaction, the concentration was 600 nM or lower. Similar methods have been used to assay this activity (Sherman and Fyfe (1990) Proc. Natl. Acad. Sci. U.S.A. 87:5119–5123; Bushman and Craigie (1991) Proc. Natl. Acad. Sci. U.S.A. 88:1339–1343)

Competition Assay.

Radioactively labeled con(+) oligo was annealed to con(–) and purified on a 8% denaturing gel. 50 nM integrase was mixed with 20 nM double-stranded con± which mimics the U5 region of the HIV genome and incubated at 37° C. for 5 minutes. After this time, varying amounts of P5 or 30N RNA (i.e., random pool RNA) was added and the reaction mix (30 µl final volume) was incubated further for 20 minutes. The reactions were then placed at room temperature and passed over nitrocellulose filters. Filters were washed three times with 1 ml of 50 mM Tris-Cl pH 7.5. Filters were dried under a heat lamp and counted in a cocktail for 1 minute each. In the absence of RNA under these conditions, approximately 10% of the double-stranded DNA was retained on filter. The buffer used in these assays was the same as the selection buffer except that the sodium chloride concentration was 180 mM.

EXAMPLE 2

Sequence Analysis.

After 18 rounds of SELEX, individual RNA molecules were isolated with increased specificity over the parent pool. Sequences cloned from round 18 selected pool fell into three major groups. The group with the highest affinity to integrase (group I) has 36 members. Eighteen clones in this group were identical and this sequence (P5) was found to be the best binder (Table 2). There are three RNA molecules in this family with a single base substitution (A15) and 2 with two bases substituted (P29). The other 13 members of group I contain 3 or more base changes (P54, P23, AND P1). There was a correlation between sequence similarity to the predominant sequence (designated P5) and affinity for integrase. Though sequence changes in general appear to preserve the structure, RNAs with fewer changes away from P5 bound better. The second group of molecules (group II) bound with an affinity which was significantly less than the group I RNAs. There are 20 members in group II of which, eight are the consensus (designated A54), four contain a single base change (P56), and the rest contain 3 or more changes (A54, P47, P64, and A11). The third grouping of sequences (group III) contains sequences which have little or no homology. However, some sequences share short sequence motifs. In addition, all of the members of group III that were tested bound significantly better than the parent pool even though binding was considerably lower than the other two groups. In general, the SELEX done at high NaCl concentration resulted in a greater number of sequences belonging to the group I class of molecules, while the SELEX experiment done at low salt gave more RNAs belonging to the group II class, which is consistent with the results from sequencing the selected pools of RNA (Table 2).

Filter Binding Studies.

Binding curves were generated for 20 different individual RNA species chosen randomly between the groups. These experiments were carried out in triplicate. All binding curves were done using $\gamma$-$^{32}$P labeled RNA in binding buffer containing 250 mM NaCl. ($K_d$ was figured from the equation $Y=M_o/(M_2+M_o)$. X $M_1$, where $M_o$=X-axis concentration value, $M_1$=maximal Y value, $M_2=K_d$, and Y=% RNA bound). The binding affinities correlate directly with the size of the groups. The highest affinity molecules are from group I, and the best binder of that group is the RNA most frequently represented, P5. The dissociation constant for P5 RNA is on the order of $12\times10^{-9}$M in binding buffer containing 250 mM NaCl. P23 has a $K_d$ of $25\times10^{-9}$M in binding buffer containing 250 mM NaCl. The $K_d$ for the parent pool of RNA under these same conditions is ~$15\times10^{-6}$M. 21-mer DNA oligos with identical sequence as the U5 terminal region of HIV-1 genome were made and used to generate binding curves. Both single-stranded and double-stranded U5 DNA bound with dissociation constants greater than $20\times10^{-6}$ (data not shown). When binding reactions were carried out in binding buffer containing 50 mM NaCl, all the dissociation constants decreased as expected. The $K_d$ of P5 RNA in 50 mM NaCl decreased to $2\times10^{-9}$M while the $K_d$ for 30N pool of RNA improved to $2.5\times10^{-8}$M. In binding buffer containing 50 mM NaCl, U5 DNA oligos bound with about the same $K_d$ as 30N RNA.

The dissociation constant for the group II RNAs is on the order of $80\times10^{-9}$M in buffer containing 250 mM NaCl. In particular, A63 had a dissociation constant of $125\times10^{-9}$M in 250 mM NaCl. RNAs taken from the third group had $K_d$ values of approximately $8\times10^{-7}$M. (A1, A2, A42, and A47 had Kd values ranging between 800 and 1000 nM). Although group IIi molecules do not show significant relatedness, all of the members that were tested bound better than the initial 30N pool.

EXAMPLE 3

PREDICTED SECONDARY STRUCTURE OF SELECTED LIGANDS

Computer Analysis of RNA Structure.

RNAs were folded using the Zucker folding program. Structures were taken with calculated folding energies $\leq-10.5$ kcal/mol. In general, related RNAs that were grouped were able to adopt similar secondary structures. The structure for P5 molecule can be formed by nearly all the members of group I (FIG. 1A). The computer-derived structure for group I RNAs appears to be quite stable. However, there are several non-canonical base pairing interactions; G18 with U52, U37 with G46 and U39 with G44 which is at the end of a stable GNRA tetra-loop. In addition, there seems to be higher-order interactions between nucleotides within loop 10 and loop 30 connected by solid lines in (FIG. 1A). The interactions between these two loops include the final non-Watson-Crick base pairing between bases U13 and C29 connected by dashes in FIG. 1A. Although this interaction is not as favorable as G-U pairing, evidence for C-U pairing in 5S Ribosomal RNA does exist (Wu and Marshall (1990) Biochem. 29:1730–1736). Since the nucleotides in loop 10 are part of the fixed sequence used for PCR amplification, there are no phylogenetic data to support the proposed interaction between the loops. The computer model for P5 folding is reasonable. Calculated free energy for this structure is -12.8 kcal/mole and other sequences with mutations away from the primary sequence can fold up with the same structure. In addition, this model is in good agreement with chemical modification data (infra). There is some ambiguity in the folding of nucleotides 36 to 48. It is probable that the nucleotides at these positions are involved in alternative structures (FIG. 1A).

The most likely computer model for group II RNAs is the stable structure calculated for A54 at -16.6 kcal/mole (FIG. 1B). The variants in this group are able to fold up into this structure. A54 has a few features that are interesting. The nucleotides at the 5' and 3' ends are single-stranded. There is a large (11 bases) purine-rich loop near the 5' end. The stems in this structure are all very G/C rich. There are four non-canonical base pairs and they are all G-U pairs. A consensus structure could not be found for members of group III.

Chemical and Enzymatic Structure Analysis.

The structure deduced for P5 RNA modified in the absence of integrase with structure-specific chemical probes and partially digested with RNases supports the computer model. Positions that were modeled as single-stranded were accessible to DMS, kethoxal and CMCT. RNase $V_1$ only showed cuts in the stem formed by nucleotides 15 to 21 and 49 to 55 (data not shown). This lends support to the computer structure since $V_1$ preferentially cleaves double-stranded RNA of length 5 base pairs or greater (Lochard and Kumar (1981) Nucleic Acids Res. 9:5125–5140; Favorova et al. (1981) Biochem. 20:1006–1011). Nucleotides 10 to 14 and 27 to 32 are modeled as being single stranded. However, the nucleotides in these loops are relatively unreactive to the modifying reagents. In addition, a putative pseudoknot can be formed between nucleotides 11 to 14 and 28 to 31. Nucleotides G10 and G32, which are single-stranded, show normal reactivity to kethoxal while G27 (also single-stranded) appears significantly less accessible. This may be a result of the interaction between the two loops. Nucleotide A43 which is modeled as being single stranded is also relatively unreactive. This base may be buried by the structure of the GNRA tetra-loop. It was not possible to study the reactivity of nucleotides 1 to 3 and 65 to 77, since we used a primer 10 bases long to anneal to the 3' end and the terminal transcript signal masks the three G's at the 5' end.

A number of positions that were accessible to modifying reagents in the absence of integrase were shielded when modification was carried out in the presence of integrase (integrase was present at concentrations of $5 \times 10^{-7}$M and $1 \times 10^{-6}$M). Nucleotides A22, A23, G27, G34, A41, G46, G48, G49 and G53 were all completely protected from attack by chemicals at $5 \times 10^{-7}$M integrase concentration. Positions G40 and G44 were partially protected at $5 \times 10^{-7}$M and showed further protection at $1 \times 10^{-6}$M. Protection by integrase can be interpreted as either direct shielding by the protein or structural perturbation of the RNA upon binding the protein. It appears the protection of residues G34, G44, G46, G49 and G53 is caused by stabilization of the RNA structure by the binding of integrase. Nucleotide A43 was minimally reactive to DMS and showed no protection by integrase, whereas the other bases in this tetra-loop were highly reactive and were strongly protected when integrase bound. It has been shown that nucleotides in GNRA tetra-loops in 16S ribosomal RNA have chemical modification patterns that are different from those of single-stranded nucleotides (Moazed et al. (1986) J. Mol. Biol. 187:399–416). In other words, whereas bases in single-stranded regions are accessible to chemical probes, tetra-loop nucleotides may form structures such that they are protected (Chastain and Tinoco (1991) Prog. Nucl. Acid. Res. and Molec. Biol. 41:131–177).

EXAMPLE 4

RNA-truncate Studies.

Truncates of P5 RNA were made to determine the minimal binding domain of the RNA. Truncated RNAs were designed based on the results from chemical protection studies. Deletion of nucleotides 1 to 6 and 64 to 77 had no noticeable effect on binding of the RNA to integrase. In addition, changing the sequence in the 3 base stem, of this truncate, which holds the 5' and 3' ends together does not affect binding. However, deleting either nucleotides 1 to 14 or 56 to 77 completely abolished binding. This result argues that there may be an interaction between the nucleotides in the loop around position 12 and position 30 that is important for binding. However, this interaction alone is not sufficient, as a stem which holds the 5' and 3' ends together is necessary. The only other argument for this interaction is that the UCUU sequence is highly conserved in the group I class of molecules even though the random region begins at position A23 and ends at G53. There is good agreement between the chemical protection data and the minimal binding domain, as all the nucleotides that are protected by integrase are within the structure that binds with the same $K_d$ as the mature molecule.

EXAMPLE 5

In Vitro Inhibition of Integrase.

When integrase was added to a reaction containing double-stranded DNA that mimics the U5 (or U3) region of HIV DNA, two nucleotides were removed from the 3' end of the strand which encodes the conserved CA near the 3' end. In a buffer containing 50 mM NaCl, about 50% of the 40 nucleotide end-labeled strand was converted to a 38 nucleotide fragment. This activity was completely inhibited by P5 at sub-micromolar concentrations (200 nM or less). Since the difference in affinity between P5 and random RNA at 50 mM NaCl was only a few fold, as expected there was no significant difference in inhibition observed with P5 and 30N at this salt concentration. Similar results were obtained at a NaCl concentration of 75 mM. P5 was selected from a random pool of 30N molecules at 250 mM NaCl. Processing activity at NaCl concentrations above 100 mM is greatly diminished.

EXAMPLE 6

Competitive Binding of P5 RNA.

Since integrase showed no processing activity at the sodium chloride concentrations at which the selections were done (i.e., 250 mM and 500 mM NaCl), competitive binding studies were carried out at a salt concentration that allows integrase to discriminate between specific and random RNAs. In binding buffer containing 180 mM NaCl, integrase was able to bind the same substrate (double-stranded con±DNA; U5 mimic) that it is able to process at 50 mM NaCl. In the 180 mM NaCl buffer, P5 inhibits 50% of the substrate binding at a concentration of 6 nM, while it took approximately 500 nM 30N RNA to provide the same extent of inhibition. Although we were not able to demonstrate directly that P5 inhibits the processing activity of integrase, it is reasonable to conclude that if integrase was functional in vitro at these salt concentrations, P5 would be a potent inhibitor. Since the $K_i$ for P5 is similar to the $K_d$, this suggests that P5 competes directly for binding with DNA substrate. Therefore, it is reasonable to conclude that under in vivo conditions where the ionic strength is much greater, P5 binds integrase with high affinity and specificity.

Blockage of integrase activities should prove to be a potent inhibitor of viral production. Similar experiments were done using HIV-1 reverse transcriptase (RT) (Tuerk et al. (1992) Proc. Natl. Acad. Sci. U.S.A. 89:6988–6992). Tuerk and Gold showed that RNAs derived from SELEX to bind RT were strong inhibitors of reverse transcription (Tuerk et al. (1992) Proc. Natl. Acad. Sci. U.S.A. 89:6988–6992) and RNase H (Chen and Gold (1994) Biochem. 33:8746–8756) activities in vitro. Thus, it is reasonable to conclude that these RNAs would have the same effect when over-expressed in vivo. One important advantage of having high affinity nucleic acid inhibitors is that these act as competitive inhibitors. Since these RNA ligands bind at the same site as DNA substrates, protein mutations that reduce the affinity of the inhibitor may also reduce the affinity of the substrate. However, the size of the RNA ligands (i.e., large relative to other inhibitors) makes them less likely to encounter mutations that confer resistance to these inhibitors, which is a major problem with the therapeutics used to combat HIV today (Larder et al. (1989) Science 243:1731–1734).

EXAMPLE 7

Modified 2'-NH$_2$Pyrimidine RNA Ligands to HIV-1 Integrase.

In order to generate ligands with improved stability in vivo, an experiment is carried out with randomized RNA containing amino (NH$_2$) functionalities at the 2'-position of each pyrimidine. A library of $10^{14}$ RNA molecules is generated that contains 30 nucleotides of contiguous random sequence flanked by defined sequences. Defined nucleotide sequences in the flanking regions of the template serve as primer annealing sites for PCR and the complement of the primer provides the T7 promoter sequence (a restriction site can be added for cloning). The random nucleotides of the initial candidate mixture are comprised of 2'—NH$_2$ pyrimidine bases. The rounds of selection and amplification are carried out as described supra in Examples 1–2 using art-known techniques.

TABLE 1 ssDNA Template

5'-GCCGGATCCGGGCCTCATGTCGAA[3 0N]TTGAGCGTTTATTCTGAGCTCCC-3'

3'PCR Primer

T7 Promotor
5'-CCGAAGCTTAATACGACTCACTATAGGGAGCTCAGAATAAACGCTCAA-3'
    HindIII

5' PCR Primer

5'-GCCGGATCCGGGCCTCATGTCGAA-3'
    Bam HI

TABLE 2

Group I

| | | Sequence | |
|---|---|---|---|
| P5 | (18) | GGGAGCUCAGAAUAAACGCUCAACCAGUCUUGUGGCUUUGAAAGAGAGAGUUCGACAUGAGGCCCGAUCCGGC | (SEQ ID NO: 1) |
| P54 | (5) | GGGAGCUCAGAAUAAACGCUCAACCAGUCUUGUGGCCAUUGAAAGAUAAGGCCGUUCGACAUGAGGCCCGAUCCGGC | (SEQ ID NO: 2) |
| P23 | (5) | GGGAGCUCAGAAUAAACGCUCAACCAGUCUAUGGGCGUUGCAAGAGAGAUAAGGGGCGUUCGACAUGAGGCCCGAUCCGGC | (SEQ ID NO: 3) |
| P1 | (3) | GGGAGCUCAGAAUAAACGCUCAACCAGUCAGUAUUAUGGCUUUGAGAGAGAGAGUUCGACAUGAGGCCCGAUCCGGC | (SEQ ID NO: 4) |
| A15 | (3) | GGGAGCUCAGAAUAAACGCUCAACCAGUCUUGUGUCCUUGUAAGAGGAGAGUUCGACAUGAGGCCCGAUCCGGC | (SEQ ID NO: 5) |
| P29 | (2) | GGGAGCUCAGAAUAAACGCUCAACCAGUCUUAUGGCAUGAAAGUGAGGAGUUCGACAUGAGGCCCGAUCCGGC | (SEQ ID NO: 6) |

Group II

| | | Sequence | |
|---|---|---|---|
| A54 | (8) | GGGAGCUCAGAAUAAACGCUCAACGGCACAGGGGGUUGUAUCCUCCGGACGAAUUCGACAUGAGGCCCGAUCCGGC | (SEQ ID NO: 7) |
| P47 | (5) | GGGAGCUCAGAAUAAACGCUCAACGGCACAGGGCCUGUAUCCUCCGGACGAAUUCGACAUGAGGCCCGAUCCGGC | (SEQ ID NO: 8) |
| P56 | (4) | GGGAGCUCAGAAUAAACGCUCAACGGCAUAGGGGGUUAUCCUCCGGACGAAUUCGACAUGAGGCCCGAUCCGGC | (SEQ ID NO: 9) |
| P64 | (2) | GGGAGCUCAGAAUAAACGCUCAACGGCAUAGGGGUGUAUCCUCCGGACGAAUUCGACAUGAGGCCCGAUCCGGC | (SEQ ID NO: 10) |
| A11 | (1) | GGGAGCUCAGAAUAAACGCUCAAGAUUGAAUGGGGGUAACCAACGGAUGAAUUCGACAUGAGGCCCGAUCCGGC | (SEQ ID NO: 11) |

Group III

| | Sequence | |
|---|---|---|
| A1 | GGGAGCUCAGAAUAAACGCUCAAGCUCAAGUCGAUGUCCAAGGCUCCUGUGCCCUAGGGCUCUCGACAUGAGGCCCGAUCCGGC | (SEQ ID NO: 12) |
| A7 | GGGAGCUCAGAAUAAACGCUCAAGCUCAAGUCAAUCGAUGUGUGCCCGAUGAAUUCGACAUGAGGCCCGAUCCGGC | (SEQ ID NO: 13) |
| P57 | GGGAGCUCAGAAUAAACGCUCAAGCUCAAGUCAAUCGAUGUCUGUGCCAUGAAUUCGACAUGAGGCCCGAUCCGGC | (SEQ ID NO: 14) |
| A29 | GGGAGCUCAGAAUAAACGCUCAAGCUCAAGUCAAUCGAUAUCGAUGUGCCCGAUGAAUUGACAUGAGGCCCGAUCCGGC | (SEQ ID NO: 15) |
| P60 | GGGAGCUCAGAAUAAACGCUCAAGCUCAAGUCAAUCGAUAUCGAUGUCGUGCCUGAUGAAUUCGACAUGAGGCCCGAUCCGGC | (SEQ ID NO: 16) |
| A25 | GGGAGCUCAGAAUAAACGCUCAAGCUCAAGUCAAUCAAAGUCGAACCAUUGAAUUGACAUGAGGCCCGAUCCGGC | (SEQ ID NO: 17) |
| P19 | GGGAGCUCAGAAUAAACGCUCAAGCUCAAGUCAAUCGCGGCCCGAUCCUAAUCCGGAUGAAUCGACAUGAGGCCCGAUCCGGC | (SEQ ID NO: 18) |
| A18 | GGGAGCUCAGAAUAAACGCUCAAGCUCAAGUCAAUCGAGGCCCGAUCCUAAUGCCAUUGAAUCGACAUGAGGCCCGAUCCGGC | (SEQ ID NO: 19) |
| A46 | GGGAGCUCAGAAUAAACGCUCAAGCUCAAGUCAAUCGAGGCCCUAAUGCCCUAAUGCCCUAGCGAAUCGACAUGAGGCCCGAUCCGGC | (SEQ ID NO: 20) |
| P55 | GGGAGCUCAGAAUAAACGCUCAAGCUCGCAUUUAGACUCGCCAUUUAGACCCUAAAUUGACAUGAGGCCCGAUCCGGC | (SEQ ID NO: 21) |
| A10 | GGGAGCUCAGAAUAAACGCUCAAGCUCAAUGUUGGUGUGAGUAAGAAAGACGAGCUCUAUAUCGACAUGAGGCCCGAUCCGGC | (SEQ ID NO: 22) |
| A23 | GGGAGCUCAGAAUAAACGCUCAAGCUCAAUGUUGGUGUAGACUCACGAUGAGCUGUGCCCCUUAUCGACAUGAGGCCCGAUCCGGC | (SEQ ID NO: 23) |
| P20 | GGGAGCUCAGAAUAAACGCUCAAGCUCAAGUCAAGGACACGAUGUGCCCGUGCCCUUUAUCGACAUGAGGCCCGAUCCGGC | (SEQ ID NO: 24) |
| P38 | GGGAGCUCAGAAUAAACGCUCAAGCUCAAUGUAGCACUAACCAUGCAAUUCGACAUGAGGCCCGAUCCGGC | (SEQ ID NO: 25) |
| A28 | GGGAGCUCAGAAUAAACGCUCAAGCUCAAUGGACACUAGAGGUGCUGUGCCUGUGCCCUUUAUUCGACAUGAGGCCCGAUCCGGC | (SEQ ID NO: 26) |
| P59 | GGGAGCUCAGAAUAAACGCUCAAGCUCAAUUGGAACUUGGAGAAGAGCCGUGCCCUCUCGACAUUCGACAUGAGGCCCGAUCCGGC | (SEQ ID NO: 27) |
| P21 | GGGAGCUCAGAAUAAACGCUCAAGCUCAAUGUUUGGAGGAGUGUGCCCUUAGACAUUCGACAUGAGGCCCGAUCCGGC | (SEQ ID NO: 28) |
| P27 | GGGAGCUCAGAAUAAACGCUCAAGCUCAAGUGUUUGGAGGAGUGUGCCCUUUAGGCAUUCGACAUGAGGCCCGAUCCGGC | (SEQ ID NO: 29) |
| P22 | GGGAGCUCAGAAUAAACGCUCAAGCUCAAUGUUGGAGGAGUGUGCCCUGACCUGAGUCUUCGACAUGAGGCCCGAUCCGGC | (SEQ ID NO: 30) |
| A14 | GGGAGCUCAGAAUAAACGCUCAAGCUCAAGUCAAGUGCCCUGAGUCUGUGCCCUGAGUCAUUUCGACAUGAGGCCCGAUCCGGC | (SEQ ID NO: 31) |
| A39 | GGGAGCUCAGAAUAAACGCUCAAGCUCAAGUCAAGUGCCCUUCCGUCCGUUCCAAUUCGACAUGAGGCCCGAUCCGGC | (SEQ ID NO: 32) |
| A64 | GGGAGCUCAGAAUAAACGCUCAAGCUCAAUGAUGUCUGCCCGGUCCGUUUCCAAUUCCGACAUGAGGCCCGAUCCGGC | (SEQ ID NO: 33) |
| P37 | GGGAGCUCAGAAUAAACGCUCAAGCUCAACCCUUUUAAUGUCCAGUUUCCAAUUUCGACAUGAGGCCCGAUCCGGC | (SEQ ID NO: 34) |
| P25 | GGGAGCUCAGAAUAAACGCUCAAGCUCAAUGGAUGUCGGUAGCGGAUCGGAUCAUCAUGAAUCGACAUGAGGCCCGAUCCGGC | (SEQ ID NO: 35) |
| P39 | GGGAGCUCAGAAUAAACGCUCAAGCUCAAUGUAGCGGAUCCUGCCGUGCCCUGUAAUGGCCAUAUGGACAUGAGGCCCGAUCCGGC | (SEQ ID NO: 36) |
| A2 | GGGAGCUCAGAAUAAACGCUCAAGCUCAAGCUAAAUGGCCAGCGUAAAGAGAGACGUAAUGCGUUCGACAUGAGGCCCGAUCCGGC | (SEQ ID NO: 37) |
| A20 | GGGAGCUCAGAAUAAACGCUCAAGCUCAACCCUCAAUGGCGUGUGGUGCAGUUGCCCUAGACACAGAUUCGACAUGAGGCCCGAUCCGGC | (SEQ ID NO: 38) |
| A48 | GGGAGCUCAGAAUAAACGCUCAAGCUCAACCCUCAAUGGUGAUGUCCCACAGUUGCCCGCACACAGGCCUAGAUUCGACAUGAGGCCCGAUCCGGC | (SEQ ID NO: 39) |
| A16 | GGGAGCUCAGAAUAAACGCUCAAGCUCAAAACGCUCCAAUCAGUUGCGAAAAUCCGACACAGGCCUAGAUUCGACAUGAGGCCCGAUCCGGC | (SEQ ID NO: 40) |
| A17 | GGGAGCUCAGAAUAAACGCUCAAGCUCAAUGCUCACACGUGUUGUGAACAGGAUUCGACAUGAGGCCCGAUCCGGC | (SEQ ID NO: 41) |
| A45 | GGGAGCUCAGAAUAAACGCUCAAGCUCAAUAUAAGCCUCACGUGUGUAUGUGCAUGGCAUGCAUGAGGCCCGAUCCGGC | (SEQ ID NO: 42) |
| A47 | GGGAGCUCAGAAUAAACGCUCAAGCUCAAGCCUCACAGGGCAUGGAAAGGUUCGACAUGAGGCCCGAUCCGGC | (SEQ ID NO: 43) |
| P42 | GGGAGCUCAGAAUAAACGCUCAAGCUCAAUCCAAUGGUGAUAUACGAUGUCGAUAUACGAUGUUCGACAUGAGGCCCGAUCCGGC | (SEQ ID NO: 44) |
| A5 | GGGAGCUCAGAAUAAACGCUCAAGCUCAAUGUCCUAACUUGCUACUGCUUGACACGUUACUGCAUGAGGCCCGAUCCGGC | (SEQ ID NO: 45) |

TABLE 2-continued

| | | |
|---|---|---|
| A55 | GGGAGCUCAGAAUAAACGCUCAAUGUCCGUUUAUGUCAAAUGUAAUUUCGUAAAUUCGACAUGAGGCCCGAUCCGGC | (SEQ ID NO: 46) |
| A9 | GGGAGCUCAGAAUAAACGCUCAAGAUCCGCAGUAAACUGAUAAUGUAAAGUACUUCGACAUGACAUGAGGCCCGAUCCGGC | (SEQ ID NO: 47) |
| A42 | GGGAGCUCAGAAUAAACGCUCAAUAGCCGGUCAAGAAAGCCGACAGUGUAUUCGACAUGAGCCAUGAGGCCCGAUCCGGC | (SEQ ID NO: 48) |
| A24 | GGGAGCUCAGAAUAAACGCUCAAGAGGCUCAACCCUUACUGCAUGCAUGGUCAAUUCGACAAUUCGAUCGACAUGAGGCCCGAUCCGGC | (SEQ ID NO: 49) |
| A53 | GGGAGCUCAGAAUAAACGCUCAAGUUCACAAGUUCCAAGAGGAAACCAUUAAUGCUAAAUUCGACAUGACAUGAGGCCCCGAUCCGGC | (SEQ ID NO: 50) |
| P32 | GGGAGCUCAGAAUAAACGCUCAACGACGUAGCGCUAAACGUAGCUUGGUGUGAAUUCGACAUGACAUGAGGCCCCGGAUCCGGC | (SEQ ID NO: 51) |
| P41 | GGGAGCUCAGAAUAAACGCUCAAUGGACUAUGGGCUAGCUCGUGGUGAAUUCGACAAUUCGACAUGAGGCCCCGGAUCCGGC | (SEQ ID NO: 52) |
| A40 | GGGAGCUCAGAAUAAACGCUCAAACCCUGACGCGGCCACGUAUAGCUAUAACUCGAUAAUUCGACAUGAGGCCCGAUCCGGC | (SEQ ID NO: 53) |
| P12 | GGGAGCUCAGAAUAAACGCUCAACCUGAGAACUGAAGCCCUCGCUCUCGUAAUUCGACAUUCGACAUGAGGCCCCGGAUCCGGC | (SEQ ID NO: 54) |
| A60 | GGGAGCUCAGAAUAAACGCUCAAGUCGACACGUACUGAGGUCGCGGAAGUAUUCGACAUGAGGCCCCGGAUCCGGC | (SEQ ID NO: 55) |

Numbers in parentheses indicate frequency of clone. Sequences with an A followed by a number were isolated from the low salt experiment, and sequences with a P followed by a number were isolated from the high salt experiment. Bases in bold type are fixed sequences used for PCR.

We claim:

1. A purified and isolated non-naturally occurring nucleic acid ligand to HIV integrase.

2. The purified and isolated non-naturally occurring nucleic acid ligand of claim 1 wherein said HIV integrase is HIV-1 integrase.

3. The purified and isolated non-naturally occurring nucleic acid ligand of claim 2 wherein said nucleic acid ligand is single-stranded.

4. The purified and isolated non-naturally occurring nucleic acid ligand of claim 3 wherein said nucleic acid ligand is RNA.

5. The purified and isolated non-naturally occurring nucleic acid ligand of claim 3 wherein said nucleic acid ligand is DNA.

6. The purified and isolated non-naturally occurring RNA ligand to HIV-1 integrase of claim 4 wherein said ligand is selected from the group consisting of the sequences set forth in Table 2.

7. The purified and isolated non-naturally occurring RNA ligand of claim 4 wherein said ligand is comprised of 2'-amino(2'-NH$_2$) modified nucleotides.

8. A nucleic acid ligand to HIV integrase identified according to the method comprising:
 a) contacting a candidate mixture of nucleic acids with HIV integrase, wherein nucleic acids having an increased affinity to HIV integrase relative to the candidate mixture may be partitioned from the remainder of the candidate mixture;
 b) partitioning the increased affinity nucleic acids from the remainder of the candidate mixture; and
 c) amplifying the increased affinity nucleic acids to yield a mixture of nucleic acids enriched for nucleic acid sequences with relatively higher affinity and specificity for binding to HIV integrase, whereby a nucleic acid ligand of HIV integrase may be identified.

9. The nucleic acid ligand of claim 8 wherein the candidate mixture contacted includes non-amplifiable random pool nucleic acids.

10. The nucleic acid ligand of claim 8 wherein said HIV integrase is HIV-1 integrase.

11. The nucleic acid ligand of claim 10 wherein said candidate mixture contacted includes non-amplifiable random pool nucleic acids.

12. The nucleic acid ligand of claim 8 wherein said ligand is an inhibitor of HIV integrase.

13. The nucleic acid ligand of claim 9 wherein said ligand is an inhibitor of HIV integrase.

14. The nucleic acid ligand of claim 10 wherein said ligand is an inhibitor of HIV-1 integrase.

15. The nucleic acid ligand of claim 11 wherein said ligand is an inhibitor of HIV-1 integrase.

16. The nucleic acid ligand of claim 11 wherein said ligand is comprised of 2'-amino (2'-NH$_2$) modified nucleotides.

* * * * *

SEQUENCE LISTING ( 1 ) GENERAL INFORMATION:

( i i i ) NUMBER OF SEQUENCES: 61

( 2 ) INFORMATION FOR SEQ ID NO:1:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGGAGCUCAG  AAUAAACGCU  CAACCAGUCU  UGUGGCUUUG  AAAGAGAGGA         50
GUGUUCGACA  UGAGGCCCGG  AUCCGGC                                    77
```

( 2 ) INFORMATION FOR SEQ ID NO:2:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
GGGAGCUCAG  AAUAAACGCU  CAACCAGUCU  UGUGGCAUUG  AAAGAUAGGU         50
GUGUUCGACA  UGAGGCCCGG  AUCCGGC                                    77
```

( 2 ) INFORMATION FOR SEQ ID NO:3:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GGGAGCUCAG  AAUAAACGCU  CAACCAGUCU  UAUGGCGUUG  CAAGAUAGGG         50
GCGUUCGACA  UGAGGCCCGG  AUCCGGC                                    77
```

( 2 ) INFORMATION FOR SEQ ID NO:4:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
GGGAGCUCAG  AAUAAACGCU  CAACCAGUAU  UAUGGCUUUG  AGAGAGAGGU         50
GCGUUCGACA  UGAGGCCCGG  AUCCGGC                                    77
```

( 2 ) INFORMATION FOR SEQ ID NO:5:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
GGGAGCUCAG  AAUAAACGCU  CAACCAGUCU  UGUGGCUUUG  UAAGAGAGGA         50
```

GUGUUCGACA UGAGGCCCGG AUCCGGC                                                77

( 2 ) INFORMATION FOR SEQ ID NO:6:

( i ) SEQUENCE CHARACTERISTICS:
           ( A ) LENGTH:77
           ( B ) TYPE: nucleic acid
           ( C ) STRANDEDNESS: single
           ( D ) TOPOLOGY: linear ( x i ) SEQUENCE DESCRIPTION: SEQ ID NO:6:

GGGAGCUCAG AAUAAACGCU CAACCAGUCU UAUGGCUUUG AAAGUGAGGA                        50

GUGUUCGACA UGAGGCCCGG AUCCGGC                                                77

( 2 ) INFORMATION FOR SEQ ID NO:7:

( i ) SEQUENCE CHARACTERISTICS:
           ( A ) LENGTH:77
           ( B ) TYPE: nucleic acid
           ( C ) STRANDEDNESS: single
           ( D ) TOPOLOGY: linear ( x i ) SEQUENCE DESCRIPTION: SEQ ID NO:7:

GGGAGCUCAG AAUAAACGCU CAACGGCACA GGGGUUGUAU CCUCCGGGAC                        50

GAAUUCGACA UGAGGCCCGG AUCCGGC                                                77

( 2 ) INFORMATION FOR SEQ ID NO:8:

( i ) SEQUENCE CHARACTERISTICS:
           ( A ) LENGTH:77
           ( B ) TYPE: nucleic acid
           ( C ) STRANDEDNESS: single
           ( D ) TOPOLOGY: linear ( x i ) SEQUENCE DESCRIPTION: SEQ ID NO:8:

GGGAGCUCAG AAUAAACGCU CAACGGCACA GGGCCUGUAU CCUCCGGGCC                        50

GAAUUCGACA UGAGGCCCGG AUCCGGC                                                77

( 2 ) INFORMATION FOR SEQ ID NO:9:

( i ) SEQUENCE CHARACTERISTICS:
           ( A ) LENGTH:77
           ( B ) TYPE: nucleic acid
           ( C ) STRANDEDNESS: single
           ( D ) TOPOLOGY: linear ( x i ) SEQUENCE DESCRIPTION: SEQ ID NO:9:

GGGAGCUCAG AAUAAACGCU CAACGGCAUA GGGGUUGUAU CCUCCGGGAC                        50

GAAUUCGACA UGAGGCCCGG AUCCGGC                                                77

( 2 ) INFORMATION FOR SEQ ID NO:10:

( i ) SEQUENCE CHARACTERISTICS:
           ( A ) LENGTH:77
           ( B ) TYPE: nucleic acid
           ( C ) STRANDEDNESS: single
           ( D ) TOPOLOGY: linear ( x i ) SEQUENCE DESCRIPTION: SEQ ID NO:10:

GGGAGCUCAG AAUAAACGCU CAACGGCACC GGGGCUGUAU CCUCCGGCAC                        50

GAAUUCGACA UGAGGCCCGG AUCCGGC                                                77

( 2 ) INFORMATION FOR SEQ ID NO:11:

( i ) SEQUENCE CHARACTERISTICS:
    ( A ) LENGTH: 75
    ( B ) TYPE: nucleic acid
    ( C ) STRANDEDNESS: single
    ( D ) TOPOLOGY: linear ( x i ) SEQUENCE DESCRIPTION: SEQ ID NO:11:

GGGAGCUCAG AAUAAACGCU CAAAGAUUGA AUGGGGUAA CCAACGGGAG      50

AUUCGACAUG AGGCCCGGAU CCGGC      75

( 2 ) INFORMATION FOR SEQ ID NO:12:

( i ) SEQUENCE CHARACTERISTICS:
    ( A ) LENGTH: 77
    ( B ) TYPE: nucleic acid
    ( C ) STRANDEDNESS: single
    ( D ) TOPOLOGY: linear ( x i ) SEQUENCE DESCRIPTION: SEQ ID NO:12:

GGGAGCUCAG AAUAAACGCU CAAGUCAAUC AUCGAUGUCC UGUGCCCUAG      50

GGCUUCGACA UGAGGCCCGG AUCCGGC      77

( 2 ) INFORMATION FOR SEQ ID NO:13:

( i ) SEQUENCE CHARACTERISTICS:
    ( A ) LENGTH: 77
    ( B ) TYPE: nucleic acid
    ( C ) STRANDEDNESS: single
    ( D ) TOPOLOGY: linear ( x i ) SEQUENCE DESCRIPTION: SEQ ID NO:13:

GGGAGCUCAG AAUAAACGCU CAAGUCAAUC UUCGAUGUGC UGUGCCCGAU      50

GAAUUCGACA UGAGGCCCGG AUCCGGC      77

( 2 ) INFORMATION FOR SEQ ID NO:14:

( i ) SEQUENCE CHARACTERISTICS:
    ( A ) LENGTH: 77
    ( B ) TYPE: nucleic acid
    ( C ) STRANDEDNESS: single
    ( D ) TOPOLOGY: linear ( x i ) SEQUENCE DESCRIPTION: SEQ ID NO:14:

GGGAGCUCAG AAUAAACGCU CAAGUCAAUC AUCGAUGUGC UGUGCCCGAU      50

AAAUUCGACA UGAGGCCCGG AUCCGGC      77

( 2 ) INFORMATION FOR SEQ ID NO:15:

( i ) SEQUENCE CHARACTERISTICS:
    ( A ) LENGTH: 77
    ( B ) TYPE: nucleic acid
    ( C ) STRANDEDNESS: single
    ( D ) TOPOLOGY: linear ( x i ) SEQUENCE DESCRIPTION: SEQ ID NO:15:

GGGAGCUCAG AAUAAACGCU CAAGUCAAUU AUCGAUGUGC UGUGCCCGAU      50

CAAUUCGACA UGAGGCCCGG AUCCGGC      77

( 2 ) INFORMATION FOR SEQ ID NO:16:

( i ) SEQUENCE CHARACTERISTICS:
    ( A ) LENGTH: 77
    ( B ) TYPE: nucleic acid
    ( C ) STRANDEDNESS: single
    ( D ) TOPOLOGY: linear ( x i ) SEQUENCE DESCRIPTION: SEQ ID NO:16:

GGGAGCUCAG AAUAAACGCU CAAGUCAAUU AUCGAUGUGC UGUGCCCGAU         50

GAAUUCGACA UGAGGCCCGG AUCCGGC         77

( 2 ) INFORMATION FOR SEQ ID NO:17:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:17:

GGGAGCUCAG AAUAAACGCU CAAGUCAAUU AUCAAAGUGC GGAACCCUAU         50

GAAUUCGACA UGAGGCCCGG AUCCGGC         77

( 2 ) INFORMATION FOR SEQ ID NO:18:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGGAGCUCAG AAUAAACGCU CAAGUCGAGG CCCGGAUGUG CUGUGCCCUG         50

GGAUUCGACA UGAGGCCCGG AUCCGGC         77

( 2 ) INFORMATION FOR SEQ ID NO:19:

( i ) SEQUENCE CHARACTERISTICS:
        ( A ) LENGTH:75
        ( B ) TYPE: nucleic acid
        ( C ) STRANDEDNESS: single
        ( D ) TOPOLOGY: linear ( x i ) SEQUENCE DESCRIPTION: SEQ ID NO:19:

GGGAGCUCAG AAUAAACGCU CAAGUCCUAA UCCCUAAUGU GAUCUGAUGA         50

AUUCGACAUG AGGCCCGGAU CCGGC         75

( 2 ) INFORMATION FOR SEQ ID NO:20:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:20:

GGGAGCUCAG AAUAAACGCU CAAGCCCCCG GUUGAAGACU UGUAAUGCCC         50

UAAUUCGACA UGAGGCCCGG AUCCGGC         77

( 2 ) INFORMATION FOR SEQ ID NO:21:

( i ) SEQUENCE CHARACTERISTICS:
        ( A ) LENGTH:78
        ( B ) TYPE: nucleic acid
        ( C ) STRANDEDNESS: single
        ( D ) TOPOLOGY: linear ( x i ) SEQUENCE DESCRIPTION: SEQ ID NO:21:

GGGAGCUCAG AAUAAACGCU CAAGUCUCGC AUUUAGACAG ACCUGUGCCC         50

```
UAAAUUCGAC AUGAGGCCCG GAUCCGGC                                              78
```

( 2 ) INFORMATION FOR SEQ ID NO:22:

( i ) SEQUENCE CHARACTERISTICS:
        ( A ) LENGTH:74
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
GGGAGCUCAG AAUAAACGCU CAAUGUUGAG UAAGACGAGC UGUGCCCUUA                      50

UUCGACAUGA GGCCCGGAUC CGGC                                                  74
```

( 2 ) INFORMATION FOR SEQ ID NO:23:

( i ) SEQUENCE CHARACTERISTICS:
        ( A ) LENGTH:75
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
GGGAGCUCAG AAUAAACGCU CAAUGGUUGU GAAAGAUGAG GUGAGCUCUU                      50

AUUCGACAUG AGGCCCGGAU CCGGC                                                 75
```

( 2 ) INFORMATION FOR SEQ ID NO:24:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
GGGAGCUCAG AAUAAACGCU CAACGCACGA CUAAGGAUGU GCUGUGCCCU                      50

UUAUUCGACA UGAGGCCCGG AUCCGGC                                               77
```

( 2 ) INFORMATION FOR SEQ ID NO:25:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
GGGAGCUCAG AAUAAACGCU CAAUGUACGA CUAAGCAUGU GCUGUGCCCU                      50

UUAUUCGACA UGAGGCCCGG AUCCGGC                                               77
```

( 2 ) INFORMATION FOR SEQ ID NO:26:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
GGGAGCUCAG AAUAAACGCU CAAUGGACAC UAGAUGAGGU GCGCUGUGCA                      50

CAUUUCGACA UGAGGCCCGG AUCCGGC                                               77
```

( 2 ) INFORMATION FOR SEQ ID NO:27:

( i ) SEQUENCE CHARACTERISTICS:
( A ) LENGTH:77
( B ) TYPE: nucleic acid
( C ) STRANDEDNESS: single
( D ) TOPOLOGY: linear ( x i ) SEQUENCE DESCRIPTION: SEQ ID NO:27:

GGGAGCUCAG AAUAAACGCU CAAUUGGAAC UCGAAAUGAU CUGCUGUGCC    50

CAUUUCGACA UGAGGCCCGG AUCCGGC    77

( 2 ) INFORMATION FOR SEQ ID NO:28:

( i ) SEQUENCE CHARACTERISTICS:
( A ) LENGTH:77
( B ) TYPE: nucleic acid
( C ) STRANDEDNESS: single
( D ) TOPOLOGY: linear ( x i ) SEQUENCE DESCRIPTION: SEQ ID NO:28:

GGGAGCUCAG AAUAAACGCU CAAUGUUUGG AGAAGAGCCG UGCCCUCUAG    50

ACAUUCGACA UGAGGCCCGG AUCCGGC    77

( 2 ) INFORMATION FOR SEQ ID NO:29:

( i ) SEQUENCE CHARACTERISTICS:
( A ) LENGTH:77
( B ) TYPE: nucleic acid
( C ) STRANDEDNESS: single
( D ) TOPOLOGY: linear ( x i ) SEQUENCE DESCRIPTION: SEQ ID NO:29:

GGGAGCUCAG AAUAAACGCU CAAUGUUUGG AGGAGAGCCG UGCCCUCUAG    50

ACAUUCGACA UGAGGCCCGG AUCCGGC    77

( 2 ) INFORMATION FOR SEQ ID NO:30:

( i ) SEQUENCE CHARACTERISTICS:
( A ) LENGTH:76
( B ) TYPE: nucleic acid
( C ) STRANDEDNESS: single
( D ) TOPOLOGY: linear ( x i ) SEQUENCE DESCRIPTION: SEQ ID NO:30:

GGGAGCUCAG AAUAAACGCU CAAGUUUGGA GGAGUGAUGU CCUCUCUAGG    50

CAUUCGACAU GAGGCCCGGA UCCGGC    76

( 2 ) INFORMATION FOR SEQ ID NO:31:

( i ) SEQUENCE CHARACTERISTICS:
( A ) LENGTH:77
( B ) TYPE: nucleic acid
( C ) STRANDEDNESS: single
( D ) TOPOLOGY: linear ( x i ) SEQUENCE DESCRIPTION: SEQ ID NO:31:

GGGAGCUCAG AAUAAACGCU CAAGAAGUGC UGUGCCCUUG ACCGUUUUAU    50

UUCUUCGACA UGAGGCCCGG AUCCGGC    77

( 2 ) INFORMATION FOR SEQ ID NO:32:

( i ) SEQUENCE CHARACTERISTICS:
( A ) LENGTH:76
( B ) TYPE: nucleic acid
( C ) STRANDEDNESS: single
( D ) TOPOLOGY: linear ( x i ) SEQUENCE DESCRIPTION: SEQ ID NO:32:

GGGAGCUCAG AAUAAACGCU CAAGAUGUGC UGUGCCCUUG AGUCGUUUCC          50

AGUUCGACAU GAGGCCCGGA UCCGGC          76

( 2 ) INFORMATION FOR SEQ ID NO:33:

( i ) SEQUENCE CHARACTERISTICS:
        ( A ) LENGTH:76
        ( B ) TYPE: nucleic acid
        ( C ) STRANDEDNESS: single
        ( D ) TOPOLOGY: linear ( x i ) SEQUENCE DESCRIPTION: SEQ ID NO:33:

GGGAGCUCAG AAUAAACGCU CAAGAUGUGC UGUGCCCUUC CUCCGUUUCC          50

AAUUCGACAU GAGGCCCGGA UCCGGC          76

( 2 ) INFORMATION FOR SEQ ID NO:34:

( i ) SEQUENCE CHARACTERISTICS:
        ( A ) LENGTH:76
        ( B ) TYPE: nucleic acid
        ( C ) STRANDEDNESS: single
        ( D ) TOPOLOGY: linear ( x i ) SEQUENCE DESCRIPTION: SEQ ID NO:34:

GGGAGCUCAG AAUAAACGCU CAAGAUGUGC UGUGCCCUUG GCCAGUUUCC          50

AAUUCGACAU GAGGCCCGGA UCCGGC          76

( 2 ) INFORMATION FOR SEQ ID NO:35:

( i ) SEQUENCE CHARACTERISTICS:
        ( A ) LENGTH:76
        ( B ) TYPE: nucleic acid
        ( C ) STRANDEDNESS: single
        ( D ) TOPOLOGY: linear ( x i ) SEQUENCE DESCRIPTION: SEQ ID NO:35:

GGGAGCUCAG AAUAAACGCU CAAUCGGUAU GUGCUGUGCC CCCGAGAGUU          50

CGUUCGACAU GAGGCCCGGA UCCGGC          76

( 2 ) INFORMATION FOR SEQ ID NO:36:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:36:

GGGAGCUCAG AAUAAACGCU CAAGCGGAUG UGCGGUGCCC UGCUUAAACG          50

UUGUUCGACA UGAGGCCCGG AUCCGGC          77

( 2 ) INFORMATION FOR SEQ ID NO:37:

( i ) SEQUENCE CHARACTERISTICS:
        ( A ) LENGTH:76
        ( B ) TYPE: nucleic acid
        ( C ) STRANDEDNESS: single
        ( D ) TOPOLOGY: linear ( x i ) SEQUENCE DESCRIPTION: SEQ ID NO:37:

GGGAGCUCAG AAUAAACGCU CAAGCGCUGC CUCAGGUAAU GCCCUUAGAA          50

AGUUCGACAU GAGGCCCGGA UCCGGC  76

( 2 ) INFORMATION FOR SEQ ID NO:38:

( i ) SEQUENCE CHARACTERISTICS:
    ( A ) LENGTH:75
    ( B ) TYPE: nucleic acid
    ( C ) STRANDEDNESS: single
    ( D ) TOPOLOGY: linear ( x i ) SEQUENCE DESCRIPTION: SEQ ID NO:38:

GGGAGCUCAG AAUAAACGCU CAAGCGAUCG ACUGCAUCAU AUGGCACGAG  50

AUUCGACAUG AGGCCCGGAU CCGGC  75

( 2 ) INFORMATION FOR SEQ ID NO:39:

( i ) SEQUENCE CHARACTERISTICS:
    ( A ) LENGTH:76
    ( B ) TYPE: nucleic acid
    ( C ) STRANDEDNESS: single
    ( D ) TOPOLOGY: linear ( x i ) SEQUENCE DESCRIPTION: SEQ ID NO:39:

GGGAGCUCAG AAUAAACGCU CAAGUGGUGA AUCAGUGCGU GUGUGGCCUA  50

GAUUCGACAU GAGGCCCGGA UCCGGC  76

( 2 ) INFORMATION FOR SEQ ID NO:40:

( i ) SEQUENCE CHARACTERISTICS:
    ( A ) LENGTH:76
    ( B ) TYPE: nucleic acid
    ( C ) STRANDEDNESS: single
    ( D ) TOPOLOGY: linear ( x i ) SEQUENCE DESCRIPTION: SEQ ID NO:40:

GGGAGCUCAG AAUAAACGCU CAAUGUCCGA AAAUCACGUU GCUGCAGACA  50

CAUUCGACAU GAGGCCCGGA UCCGGC  76

( 2 ) INFORMATION FOR SEQ ID NO:41:

( i ) SEQUENCE CHARACTERISTICS:
    ( A ) LENGTH:77
    ( B ) TYPE: nucleic acid
    ( C ) STRANDEDNESS: single
    ( D ) TOPOLOGY: linear ( x i ) SEQUENCE DESCRIPTION: SEQ ID NO:41:

GGGAGCUCAG AAUAAACGCU CAAACAUCGA UGACCGGAAU GCCGCACACA  50

GAGUUCGACA UGAGGCCCGG AUCCGGC  77

( 2 ) INFORMATION FOR SEQ ID NO:42:

( i ) SEQUENCE CHARACTERISTICS:
    ( A ) LENGTH:76
    ( B ) TYPE: nucleic acid
    ( C ) STRANDEDNESS: single
    ( D ) TOPOLOGY: linear ( x i ) SEQUENCE DESCRIPTION: SEQ ID NO:42:

GGGAGCUCAG AAUAAACGCU CAAUAAGCCU CACGUUUGUC UGAACAGGAU  50

CGUUCGACAU GAGGCCCGGA UCCGGC  76

( 2 ) INFORMATION FOR SEQ ID NO:43:

( i ) SEQUENCE CHARACTERISTICS:
    ( A ) LENGTH: 76
    ( B ) TYPE: nucleic acid
    ( C ) STRANDEDNESS: single
    ( D ) TOPOLOGY: linear ( x i ) SEQUENCE DESCRIPTION: SEQ ID NO:43:

| | | | | | |
|---|---|---|---|---|---|
| GGGAGCUCAG | AAUAAACGCU | CAAGCCUCAC | UGUUGUAUUG | UGCCGCAUGG | 50 |
| CAUUCGACAU | GAGGCCCGGA | UCCGGC | | | 76 |

( 2 ) INFORMATION FOR SEQ ID NO:44:

( i ) SEQUENCE CHARACTERISTICS:
    ( A ) LENGTH: 75
    ( B ) TYPE: nucleic acid
    ( C ) STRANDEDNESS: single
    ( D ) TOPOLOGY: linear ( x i ) SEQUENCE DESCRIPTION: SEQ ID NO:44:

| | | | | | |
|---|---|---|---|---|---|
| GGGAGCUCAG | AAUAAACGCU | CAAUCCAUGU | UCGAUAUACA | GGAUGGAAAG | 50 |
| GUUCGACAUG | AGGCCCGGAU | CCGGC | | | 75 |

( 2 ) INFORMATION FOR SEQ ID NO:45:

( i ) SEQUENCE CHARACTERISTICS:
    ( A ) LENGTH: 76
    ( B ) TYPE: nucleic acid
    ( C ) STRANDEDNESS: single
    ( D ) TOPOLOGY: linear ( x i ) SEQUENCE DESCRIPTION: SEQ ID NO:45:

| | | | | | |
|---|---|---|---|---|---|
| GGGAGCUCAG | AAUAAACGCU | CAAUGUCCUU | AACUUGCUAC | UUCACGCUGU | 50 |
| ACUUCGACAU | GAGGCCCGGA | UCCGGC | | | 76 |

( 2 ) INFORMATION FOR SEQ ID NO:46:

( i ) SEQUENCE CHARACTERISTICS:
    ( A ) LENGTH: 77
    ( B ) TYPE: nucleic acid
    ( C ) STRANDEDNESS: single
    ( D ) TOPOLOGY: linear ( x i ) SEQUENCE DESCRIPTION: SEQ ID NO:46:

| | | | | | |
|---|---|---|---|---|---|
| GGGAGCUCAG | AAUAAACGCU | CAAUGUCCGU | UUUAUGUCAA | AUGUAUUUCG | 50 |
| UAAUUCGACA | UGAGGCCCGG | AUCCGGC | | | 77 |

( 2 ) INFORMATION FOR SEQ ID NO:47:

( i ) SEQUENCE CHARACTERISTICS:
    ( A ) LENGTH: 77
    ( B ) TYPE: nucleic acid
    ( C ) STRANDEDNESS: single
    ( D ) TOPOLOGY: linear ( x i ) SEQUENCE DESCRIPTION: SEQ ID NO:47:

| | | | | | |
|---|---|---|---|---|---|
| GGGAGCUCAG | AAUAAACGCU | CAAGAUCCGC | AGUAACUGAU | AAUGUUAAAG | 50 |
| UACUUCGACA | UGAGGCCCGG | AUCCGGC | | | 77 |

( 2 ) INFORMATION FOR SEQ ID NO:48:

( i ) SEQUENCE CHARACTERISTICS:
    ( A ) LENGTH: 77
    ( B ) TYPE: nucleic acid
    ( C ) STRANDEDNESS: single
    ( D ) TOPOLOGY: linear ( x i ) SEQUENCE DESCRIPTION: SEQ ID NO:48:

GGGAGCUCAG AAUAAACGCU CAAUAGCCGG GUCAAGAAAG CCGGACAGUG    50

UUAUUCGACA UGAGGCCCGG AUCCGGC    77

( 2 ) INFORMATION FOR SEQ ID NO:49:

( i ) SEQUENCE CHARACTERISTICS:
        ( A ) LENGTH:77
        ( B ) TYPE: nucleic acid
        ( C ) STRANDEDNESS: single
        ( D ) TOPOLOGY: linear ( x i ) SEQUENCE DESCRIPTION: SEQ ID NO:49:

GGGAGCUCAG AAUAAACGCU CAAGAGGCUC AACCCUUACU GCAUGCUGGU    50

CAAUUCGACA UGAGGCCCGG AUCCGGC    77

( 2 ) INFORMATION FOR SEQ ID NO:50:

( i ) SEQUENCE CHARACTERISTICS:
        ( A ) LENGTH:75
        ( B ) TYPE: nucleic acid
        ( C ) STRANDEDNESS: single
        ( D ) TOPOLOGY: linear ( x i ) SEQUENCE DESCRIPTION: SEQ ID NO:50:

GGGAGCUCAG AAUAAACGCU CAAGUUCACA AGAGGAAACC AUUAAUGCUA    50

AUUCGACAUG AGGCCCGGAU CCGGC    75

( 2 ) INFORMATION FOR SEQ ID NO:51:

( i ) SEQUENCE CHARACTERISTICS:
        ( A ) LENGTH:74
        ( B ) TYPE: nucleic acid
        ( C ) STRANDEDNESS: single
        ( D ) TOPOLOGY: linear ( x i ) SEQUENCE DESCRIPTION: SEQ ID NO:51:

GGGAGCUCAG AAUAAACGCU CAACGACGCU AAACGUAGCU UGGUUGUGUA    50

UUCGACAUGA GGCCCGGAUC CGGC    74

( 2 ) INFORMATION FOR SEQ ID NO:52:

( i ) SEQUENCE CHARACTERISTICS:
        ( A ) LENGTH:74
        ( B ) TYPE: nucleic acid
        ( C ) STRANDEDNESS: single
        ( D ) TOPOLOGY: linear ( x i ) SEQUENCE DESCRIPTION: SEQ ID NO:52:

GGGAGCUCAG AAUAAACGCU CAAUGACUAU GGGCUAGACU GCUUGGUGAA    50

UUCGACAUGA GGCCCGGAUC CGGC    74

( 2 ) INFORMATION FOR SEQ ID NO:53:

( i ) SEQUENCE CHARACTERISTICS:
        ( A ) LENGTH:76
        ( B ) TYPE: nucleic acid
        ( C ) STRANDEDNESS: single
        ( D ) TOPOLOGY: linear ( x i ) SEQUENCE DESCRIPTION: SEQ ID NO:53:

GGGAGCUCAG AAUAAACGCU CAAACCCCUG ACGCGCACGU AUAGCUGACU    50

AAUUCGACAU GAGGCCCGGA UCCGGC                                                    76

(2) INFORMATION FOR SEQ ID NO:54:

(i) SEQUENCE CHARACTERISTICS:
        (A) LENGTH:77
        (B) TYPE: nucleic acid
        (C) STRANDEDNESS: single
        (D) TOPOLOGY: linear (xi) SEQUENCE DESCRIPTION: SEQ ID NO:54:

GGGAGCUCAG AAUAAACGCU CAACCUGAGA ACUGAAGCCC UCGUCUGCCG                          50

UAAUUCGACA UGAGGCCCGG AUCCGGC                                                   77

(2) INFORMATION FOR SEQ ID NO:55:

(i) SEQUENCE CHARACTERISTICS:
        (A) LENGTH:75
        (B) TYPE: nucleic acid
        (C) STRANDEDNESS: single
        (D) TOPOLOGY: linear (xi) SEQUENCE DESCRIPTION: SEQ ID NO:55:

GGGAGCUCAG AAUAAACGCU CAAGUCGACA CGUACUGAGG UCGCGGAAGU                          50

AUUCGACAUG AGGCCCGGAU CCGGC                                                     75

(2) INFORMATION FOR SEQ ID NO:56:

(i) SEQUENCE CHARACTERISTICS:
        (A) LENGTH:40
        (B) TYPE: nucleic acid
        (C) STRANDEDNESS: single
        (D) TOPOLOGY: linear (xi) SEQUENCE DESCRIPTION: SEQ ID NO:56:

CAATGACCGC ATGGGATCCG TGTGGAAAAT CTCTAGCAGT                                     40

(2) INFORMATION FOR SEQ ID NO:57:

(i) SEQUENCE CHARACTERISTICS:
        (A) LENGTH:77
        (B) TYPE: nucleic acid
        (C) STRANDEDNESS: single
        (D) TOPOLOGY: linear (xi) SEQUENCE DESCRIPTION: SEQ ID NO:57:

GCCGGATCCG GGCCTCATGT CGAANNNNNN NNNNNNNNNN NNNNNNNNNN                          50

NNNNTTGAGC GTTTATTCTG AGCTCCC                                                   77

(2) INFORMATION FOR SEQ ID NO:58:

(i) SEQUENCE CHARACTERISTICS:
        (A) LENGTH:48
        (B) TYPE: nucleic acid
        (C) STRANDEDNESS: single
        (D) TOPOLOGY: linear (xi) SEQUENCE DESCRIPTION: SEQ ID NO:58:

CCGAAGCTTA ATACGACTCA CTATAGGGAG CTCAGAATAA ACGCTCAA                            48

(2) INFORMATION FOR SEQ ID NO:59:

(i) SEQUENCE CHARACTERISTICS:
        (A) LENGTH:24
        (B) TYPE: nucleic acid (C) STRANDEDNESS: single
(D) TOPOLOGY: linear (xi) SEQUENCE DESCRIPTION: SEQ ID NO:59:

GCCGGATCCG GGCCTCATGT CGAA          24

(2) INFORMATION FOR SEQ ID NO:60:

(i) SEQUENCE CHARACTERISTICS:
(A) LENGTH:25
(B) TYPE: nucleic acid
(C) STRANDEDNESS: single
(D) TOPOLOGY: linear (xi) SEQUENCE DESCRIPTION: SEQ ID NO:60:

CCCGGATCCT CTTTACCTCT GTGTG          25

(2) INFORMATION FOR SEQ ID NO:61:

(i) SEQUENCE CHARACTERISTICS:
(A) LENGTH:49
(B) TYPE: nucleic acid
(C) STRANDEDNESS: single
(D) TOPOLOGY: linear (xi) SEQUENCE DESCRIPTION: SEQ ID NO:61:

CCGAAGCTTA ATACGACTCA CTATAGGGAC TATTGATGGC CTTCCGACC          49